US008057478B2

(12) United States Patent
Kuczynski et al.

(10) Patent No.: US 8,057,478 B2
(45) Date of Patent: Nov. 15, 2011

(54) UNICONDYLAR KNEE INSTRUMENT SYSTEM

(75) Inventors: John D. Kuczynski, Pequannock, NJ (US); Mikhail Kvitnitsky, Clifton, NJ (US)

(73) Assignee: Arthrex, Inc., Naples, FL (US)

(*) Notice: Subject to any disclaimer, the term of this patent is extended or adjusted under 35 U.S.C. 154(b) by 242 days.

(21) Appl. No.: 12/541,676

(22) Filed: Aug. 14, 2009

(65) Prior Publication Data
US 2009/0306670 A1 Dec. 10, 2009

Related U.S. Application Data

(62) Division of application No. 11/338,159, filed on Jan. 23, 2006, now Pat. No. 7,601,154.

(60) Provisional application No. 60/672,211, filed on Apr. 18, 2005.

(51) Int. Cl.
*A61F 2/46* (2006.01)
(52) U.S. Cl. ............................. 606/88; 606/86 R; 606/87
(58) Field of Classification Search ............... 606/86 R, 606/87, 88, 90, 102, 105
See application file for complete search history.

(56) References Cited

U.S. PATENT DOCUMENTS

| 4,699,129 A | 10/1987 | Aaserude et al. |
| 4,714,474 A | 12/1987 | Brooks, Jr. et al. |
| 4,719,908 A | 1/1988 | Averill et al. |
| 4,795,468 A | 1/1989 | Hodorek et al. |
| 4,935,023 A | 6/1990 | Whiteside et al. |
| 4,938,769 A | 7/1990 | Shaw |
| 4,963,153 A | 10/1990 | Noesberger et al. |
| 5,037,439 A | 8/1991 | Albrektsson et al. |
| 5,074,880 A | 12/1991 | Mansat |
| 5,122,144 A | 6/1992 | Bert et al. |
| 5,171,276 A | 12/1992 | Caspari et al. |
| 5,197,944 A | 3/1993 | Steele |
| 5,201,768 A | 4/1993 | Caspari et al. |
| 5,203,807 A | 4/1993 | Evans et al. |
| 5,207,711 A | 5/1993 | Caspari et al. |
| 5,306,276 A | 4/1994 | Johnson et al. |
| 5,312,411 A | 5/1994 | Steele et al. |
| 5,314,482 A | 5/1994 | Goodfellow et al. |
| 5,326,361 A | 7/1994 | Hollister |
| 5,336,266 A | 8/1994 | Caspari et al. |
| 5,609,643 A | 3/1997 | Colleran et al. |
| 5,628,749 A | 5/1997 | Vendrely et al. |
| 5,643,272 A | 7/1997 | Haines et al. |
| 5,788,700 A | 8/1998 | Morawa et al. |
| 5,871,546 A | 2/1999 | Colleran et al. |
| 5,908,424 A | 6/1999 | Bertin et al. |
| 6,024,746 A | 2/2000 | Katz |

(Continued)

OTHER PUBLICATIONS

Office Action for co-pending U.S. Appl. No. 11/338,159, dated Apr. 16, 2008.

(Continued)

*Primary Examiner* — Thomas Barrett
*Assistant Examiner* — Ellen C Hammond
(74) *Attorney, Agent, or Firm* — Carlson, Gaskey & Olds, P.C.

(57) ABSTRACT

The present invention provides for an apparatus for cutting a tibia, a stylus, an apparatus for cutting a femur, an apparatus for aligning a femoral cutting guide, and an ankle clamp in support of a unicondylar knee surgery. The present invention further provides for a method of preparing a femoral condyle of a femur for the implantation of a unicondylar femoral knee implant. The apparatus for cutting a tibia includes a unicondylar tibial resection guide that is adjustably connectable to a unicondylar tibial alignment guide and configured to operate concurrently with the tibial alignment guide. The apparatus for cutting a femur includes a spacer block and a cutting guide configured to operate concurrently with the spacer block.

9 Claims, 17 Drawing Sheets

U.S. PATENT DOCUMENTS

| | | |
|---|---|---|
| 6,059,831 A | 5/2000 | Braslow et al. |
| 6,077,270 A | 6/2000 | Katz |
| 6,090,114 A | 7/2000 | Matsuno et al. |
| 6,093,205 A | 7/2000 | McLeod et al. |
| 6,165,222 A | 12/2000 | Hoeppner et al. |
| 6,221,035 B1 | 4/2001 | Kana et al. |
| 6,267,762 B1 | 7/2001 | Millard et al. |
| 6,296,646 B1 | 10/2001 | Williamson |
| 6,468,280 B1 | 10/2002 | Saenger et al. |
| 6,478,799 B1 | 11/2002 | Williamson |
| 6,494,914 B2 | 12/2002 | Brown et al. |
| 6,554,838 B2 | 4/2003 | McGovern et al. |
| 6,569,202 B2 | 5/2003 | Whiteside |
| 6,673,077 B1 | 1/2004 | Katz |
| 6,770,077 B2 | 8/2004 | Van Zile et al. |
| 6,797,006 B2 | 9/2004 | Hodorek |
| 6,869,448 B2 | 3/2005 | Tuke et al. |
| 6,942,700 B2 | 9/2005 | Williamson |
| 7,060,074 B2 | 6/2006 | Rosa et al. |
| 7,172,597 B2 | 2/2007 | Sanford |
| 7,335,206 B2 | 2/2008 | Steffensmeier et al. |
| 7,377,924 B2 | 5/2008 | Raistrick et al. |
| 2002/0068979 A1 | 6/2002 | Brown et al. |
| 2002/0133164 A1 | 9/2002 | Williamson |
| 2002/0183760 A1 | 12/2002 | McGovern et al. |
| 2003/0014122 A1 | 1/2003 | Whiteside |
| 2003/0100907 A1 | 5/2003 | Rosa et al. |
| 2003/0100953 A1 | 5/2003 | Rosa et al. |
| 2003/0130665 A1 | 7/2003 | Pinczewski et al. |
| 2003/0139817 A1 | 7/2003 | Tuke et al. |
| 2003/0153923 A1 | 8/2003 | Pinczewski et al. |
| 2003/0233149 A1 | 12/2003 | Hodorek |
| 2004/0006394 A1 | 1/2004 | Lipman et al. |
| 2004/0102852 A1 | 5/2004 | Johnson et al. |
| 2004/0153164 A1 | 8/2004 | Sanford et al. |
| 2004/0249386 A1 | 12/2004 | Faoro |
| 2004/0249387 A1 | 12/2004 | Faoro |
| 2005/0085920 A1 | 4/2005 | Williamson |
| 2005/0125068 A1 | 6/2005 | Hozack et al. |
| 2005/0143746 A1 | 6/2005 | Steffensmeier et al. |
| 2005/0171604 A1 | 8/2005 | Michalow |

OTHER PUBLICATIONS

Office Action for co-pending U.S. Appl. No. 11/338,159, dated Sep. 4, 2008.

Office Action for co-pending U.S. Appl. No. 11/338,159, dated Jan. 13, 2009.

Office Action for co-pending U.S. Appl. No. 11/338,159, dated Jun. 17, 2009.

Office Action for co-pending U.S. Appl. No. 11/304,958, dated Jan. 4, 2007.

Office Action for co-pending U.S. Appl. No. 11/304,958, dated Jul. 18, 2007.

Advisory Action for co-pending U.S. Appl. No. 11/304,958, dated Oct. 25, 2007.

Office Action for co-pending U.S. Appl. No. 11/304,958, dated Mar. 17, 2008.

Office Action for co-pending U.S. Appl. No. 11/304,958, dated Oct. 17, 2008.

International Search Report and Written Opinion of PCT/US06/02907, Apr. 4, 2007.

Harrington, Ian J., Static and Dynamic Loading Patterns in Knee Joints with Deformities. The Journal of Bone and Joint Surgery, Incorporated vol. 65-A, No. 2, Feb. 1983, 247-259.

International Preliminary Report and Written Opinion of PCT/US06/02907.

Distal (Extension)

Damaged Surface

Posterior (Flexion)

Distal (Extension)

Posterior (Flexion)

Damaged Surface

UNICONDYLAR KNEE INSTRUMENT SYSTEM

CROSS REFERENCE TO RELATED APPLICATIONS

The present application is a divisional application of U.S. application Ser. No. 11/338,159, filed Jan. 23, 2006, now U.S. Pat. No. 7,601,154, and entitled "UNICONDYLAR KNEE INSTRUMENT SYSTEM", which claims the benefit of Provisional Application No. 60/672,211 filed Apr. 18, 2005, the entire disclosures of which are incorporated herein by reference.

BACKGROUND OF THE INVENTION

1. Field of the Invention

The present invention is related to orthopedic surgical instrumentation. In particular, the present invention is related to a unicondylar knee instrument system and a method of preparing a distal femur for the implantation of a unicondylar femoral implant.

2. Description of the Related Art

Orthopedic knee implant systems have been used for many years to treat patients with knee joints that have been damaged by trauma or disease, such as osteoarthritis, rheumatoid arthritis, and avascular neurosis. A knee arthroplasty resects, cuts, or resurfaces the damaged sections of the knee and replaces them with a prosthetic implant.

Most knee implant systems are tricompartmental implants and the surgical procedure used with tricompartmental implants is commonly known as total knee arthroplasty. These implants are known as tricompartmental implants because they are used when the femur is prepared to receive an implant by resurfacing or resecting the three compartments of the distal femur, i.e., the medial and lateral condyles and the trochlear groove. Regardless of the type of implant used, all arthroplasties require the bone to be specifically prepared to receive a corresponding implant by resecting, resurfacing, or deforming the bone to accept the implant.

Minimally invasive surgery ("MIS") has become of great interest within the field of orthopedics. Thus, unicondylar or unicompartmental knee implants have become of great interest in the orthopedic industry due to their small size and applicability to MIS surgical approaches. Unicondylar knee implants are designed to replace only a single condyle (e.g., the medial or lateral condyle) of the distal femur.

Minimally invasive knee surgery has not yet been fully defined. However, minimally invasive knee surgery has generally been considered to include a smaller incision. A typical incision length for a total knee replacement can be up to 10 to 12 inches long. The general theory behind MIS is that with a smaller incision length, the patient will be able to recover from surgery faster.

Generally, the clinical outcomes for unicondylar knee implants have varied. Studies have reported long term survival rates for unicondylar implants to be less than that of comparable total knee implants. One particular cause for such discrepancies is due to the surgical technique associated with implanting the implant.

The unicompartmental implant most widely reported on is the Oxford implant. The Oxford implant is a mobile bearing unicompartmental implant that is implanted with a free-hand technique, i.e., where the bone resections are not guided by instrumentation. Thus, the clinical outcomes for these implants have in part been associated with a particular surgeon's ability in implanting the device. Accordingly, a surgeon proficient in this technique is more likely to have a better surgical outcome compared to a less experienced surgeon who is less technically proficient with the surgical technique for implanting the implant.

Recent advancements in unicondylar knee implants and instruments have resulted in instrumented techniques for implantation. U.S. Pat. No. 6,554,838 to McGovern et al. discloses a unicondylar knee implant that uses a guided burring technique to implant the femoral component. However, conventional instrumentation systems are bulky and are required to be operated from various angles as opposed to a single orientation. Such instrument designs are also not completely conducive to minimally invasive surgical approaches or a reproducible surgical result.

Thus, there is a need for a unicompartmental knee instrument system that addresses the above mentioned deficiencies in current instrument designs while simultaneously being suitable for minimally invasive surgical techniques.

BRIEF SUMMARY OF THE INVENTION

The present invention provides for an apparatus for cutting a tibia in support of a unicondylar knee surgery that includes a unicondylar tibial alignment guide having a tibia anchor and a unicondylar tibial resection guide adjustably connectable to the unicondylar tibial alignment guide and configured to operate concurrently with the unicondylar tibial alignment guide that includes, an extended arm having at least one cutting guide surface, and a tibial resection guide base connected to the extended arm. The apparatus can further include an extended arm such that the extended arm is the only element of the unicondylar tibial resection guide within a wound area and wherein the unicondylar tibial resection guide is adjustable in three degrees of freedom. The three degrees of freedom are heaving, pitching, and rolling. In addition, the apparatus can be configured with an overall thickness of the extended arm to be about 1 to about 100 mm thick and preferably about 2 to about 5 mm thick. Moreover, the unicondylar tibial alignment guides includes at least two telescoping sections and a screw clamp connected to the tibial resection guide base attaching the unicondylar tibial resection guide to the unicondylar tibial alignment guide.

The present invention also provides for a tibial stylus for use in support of a unicondylar knee surgery that includes a tibial stylus pointer, a member having an open top surface, and a tibial stylus base. The tibial stylus base has a posterior end configured to slidingly engage along the open top surface and an elongated anterior end connectable to the tibial stylus configured such that the tibial stylus pointer moves along the anterior end of the tibial stylus base. The member can be a unicondylar tibial resection guide having an extended arm having at least one cutting surface and a tibial resection guide base connected to the extended arm. The posterior end of the tibial stylus base can be U-shaped.

The present invention also provides for an apparatus for cutting a femur in support of a unicondylar knee surgery including an instrument handle assembly having an elongated handle having a base and a spacer block removably connectable to the base, and a unicondylar resection guide removably connectable to the base and configured to operate concurrently with the space block. The unicondylar resection guide has at least one channel for guiding a cutting tool and at least one opening for receiving a fixing element. The unicondylar resection guide can also be configured to be slidingly and removably connectable to the base. Moreover, the spacer block and unicondylar resection guide can be configured to operate independently of each other.

The present invention further provides for an apparatus for aligning a unicondylar femoral cutting guide for use in support of a unicondylar knee surgery that includes an instrument handle assembly having a base and an alignment rod holder connected to the instrument handle assembly that slides substantially in the medial and lateral direction. This apparatus can further include a unicondylar resection guide removably connectable to the base or a unicondylar resection guide slidingly and removably connectable to the base or a spacer block removably connectable to the base. The alignment rod holder includes a first alignment rod holder base having at least one substantially vertical passage, a second alignment rod holder base having at least one substantially vertical passage, and at least one dowel connecting the first and second alignment rod holder bases such that the first and second alignment rod holder bases slide within the instrument handle assembly in a substantially medial and lateral direction.

The present invention also provides for an ankle clamp for supporting an apparatus for cutting a tibia in support of a unicondylar knee surgery that includes an ankle clamp base that includes a pair of base arms, each having a slot, a pair of clamping arms, each having a slot and pivotably connected to the pair of base arms, and a pair of springs, each respectively connecting the base arm and the clamping arm such that an opening force is provided to open the clamping arms. The pair of springs can also be configured to provide a clamping force to close the clamping arms. The pair of springs is connected to a pair of dowels respectively, offset a predetermined distance from the pivotable connection of the clamping arms and base arms. The ankle clamp can further include a unicondylar tibial alignment guide connected to the ankle clamp base.

The present invention further provides for a method of preparing a femoral condyle of a femur for the implantation of a unicondylar femoral knee implant which includes the steps of, resecting a tibia, determining a least affected site, wherein the site is a distal femoral condyle or a posterior femoral condyle, positioning the knee such that the least affected site faces the tibia, positioning a spacer block between the resected tibia and the least affected site, determining an overall thickness for balancing the knee and resecting the femur to a thickness of a corresponding unicondylar femoral implant, determining a spacer block and unicondylar femoral cutting block combination that equals the overall thickness when the knee is in extension, and resecting the distal femoral condyle.

BRIEF DESCRIPTION OF THE DRAWINGS

Further aspects and advantages of the invention will become apparent from the following description and claims, and from the accompanying drawings, wherein:

DETAILED DESCRIPTION OF THE INVENTION

As used herein, the following definitional terms apply. The term "unicondylar" is synonymous with "unicompartmental." "Anterior" and "posterior" mean nearer to the front or the back of the body respectively. "Proximal" and "distal" mean nearer and farther from the center of the body respectively. "Medial" and "lateral" mean nearer or farther from the median plane respectively. The median plane is an imaginary, vertical plane that divides the body into a right and left half. The coronal plane is an imaginary, vertical plane that divides the body into a front half and a back half. "Superior" and "inferior" mean above or below respectively. For example, the distal femur has medial and lateral condyles that are superior to the proximal tibia. "Sagittal" means a side profile. Varus means turned inward and valgus means turned outward or away from the body. The terms "resection guide", "cutting guide", "resection block", and "cutting block" are used synonymously.

The present unicondylar knee instrument system can be used for implanting a unicondylar knee prosthesis in either the medial or lateral condyle of the left or right knee.

Figure 1:
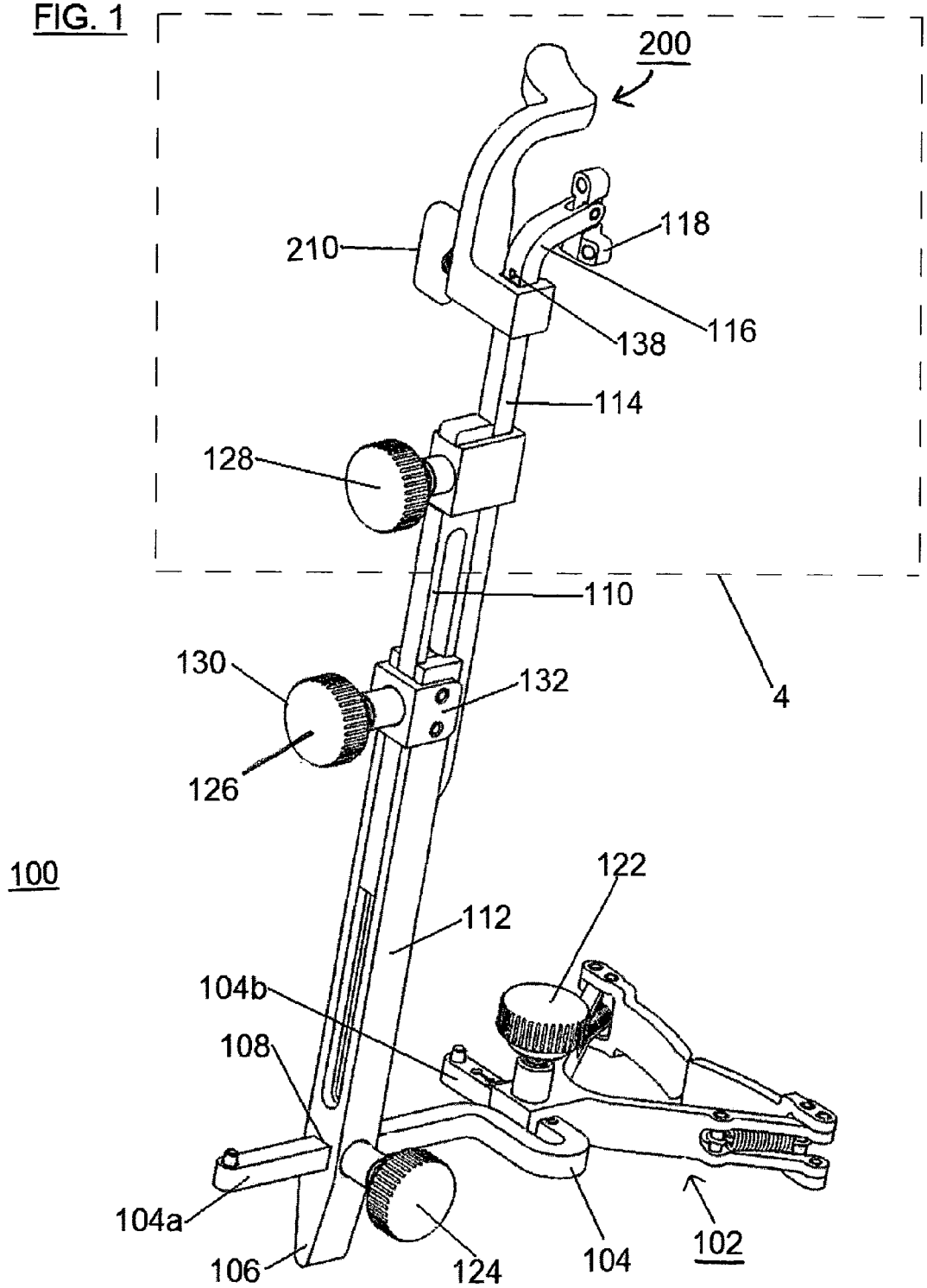
FIG. 1 is a perspective view of an embodiment of a unicondylar tibial alignment guide assembled to a unicondylar tibial resection guide of the present invention.

FIG. 1 illustrates an embodiment of a unicondylar tibial alignment guide 100 assembled to a unicondylar tibial resection guide 200. The unicondylar tibial alignment guide 100 can be provided with an ankle clamp 102, a connecting rod 104, a bottom sliding section 112, a middle sliding section 110, a top sliding section 114, a pivoting tibia anchor 118, a varus/valgus clamp 122, a flexion/extension clamp 124, a middle slide clamp 126, and a top slide clamp 128. The bottom sliding section 112 can be configured with a metatarsal pointer 106. The unicondylar tibial resection guide 200 attaches to the top sliding section 114 as shown. The unicondylar tibial resection guide 200 is adjustably connectable to the unicondylar tibial alignment guide 100 and configured to operate concurrently with the unicondylar tibial alignment guide 100.

The ankle clamp 102 may be attached to an ankle by spring loaded arms, elastic straps, extension springs, or other like devices known in the art. The ankle clamp 102 has a varus/valgus clamp 122 about which a connecting rod 104 slides in a substantially medial/lateral direction.

Figure 2:
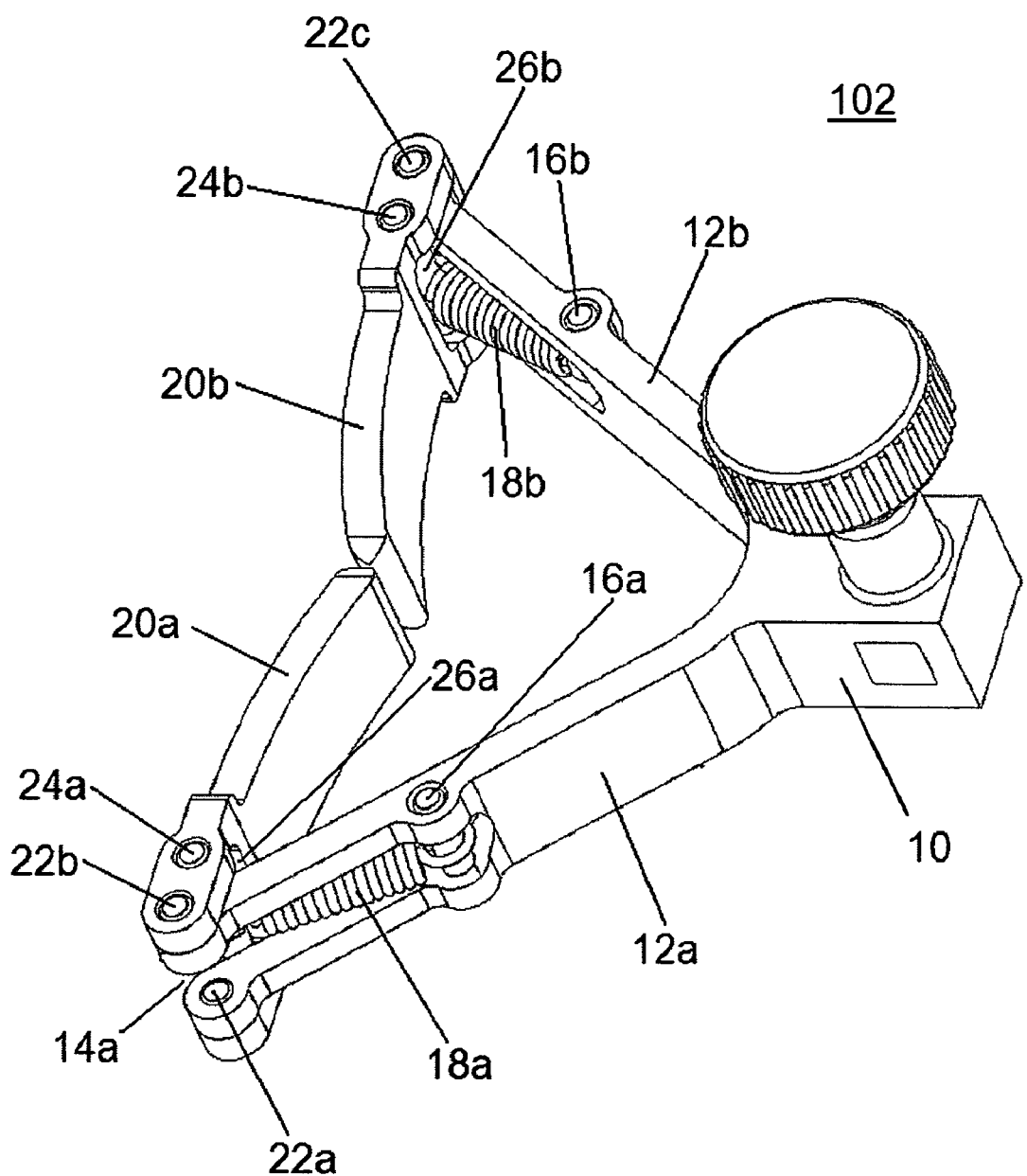
FIG. 2 is a perspective view of an ankle clamp of the unicondylar tibial alignment guide of FIG. 1.

As further detailed in FIG. 2, the ankle clamp 102 includes an ankle clamp base 10, a pair of base arms 12a, 12b, a pair of clamping arms 20a, 20b and a pair of springs 18a, 18b connected to the base arms 12a, 12b and the pair of clamping arms 20a, 20b. The base arms 12a, 12b each has a slot or opening 14a, 14b (not shown) for a spring to pass through. At one end of the slot, for example 14a, is connected a dowel 16a upon which one end of the spring 18a is attached. The other end of the slot 14a is connected to the clamping arm 20a by a pair of pins 22a, 22b such that the clamping arm 20a pivots about the pins 22a, 22b. The opposing end of the spring 18a is connected to a dowel 24a that is offset a certain distance from the pins 22a, 22b along the clamping arm 20a having a slot or opening 26a for the spring 18a to pass through. The opposing base arm 12b, clamping arm 20b, and spring 18b are configured in the same manner as base arm 12a, clamping arm 20a, and spring 18a. The slots 14a, 14b & 26a, 26b of the base arms and clamping arms along with the offset dowels 24a, 24b allow the clamping arms 20a, 20b to toggle about pins 22a, 22b & 22c, 22d as a result of springs 18a, 18b.

The springs 18a, 18b connect the clamping arms 20a, 20b to the ankle clamp base 10 such that the springs constantly provides a force to open the clamping arms 20a, 20b. In addition, the springs 18a, 18b can also be configured to provide a clamping force to close the clamping arms 20a, 20b around the ankle of a patient. It is understood that the ankle clamp 102 can clamp over the patient's ankle that is completely covered by soft tissue as well as surgical wrap. The present ankle clamp embodiment advantageously allows the instrument to be easily cleaned and steam sterilized as a result of its design.

Figure 3:
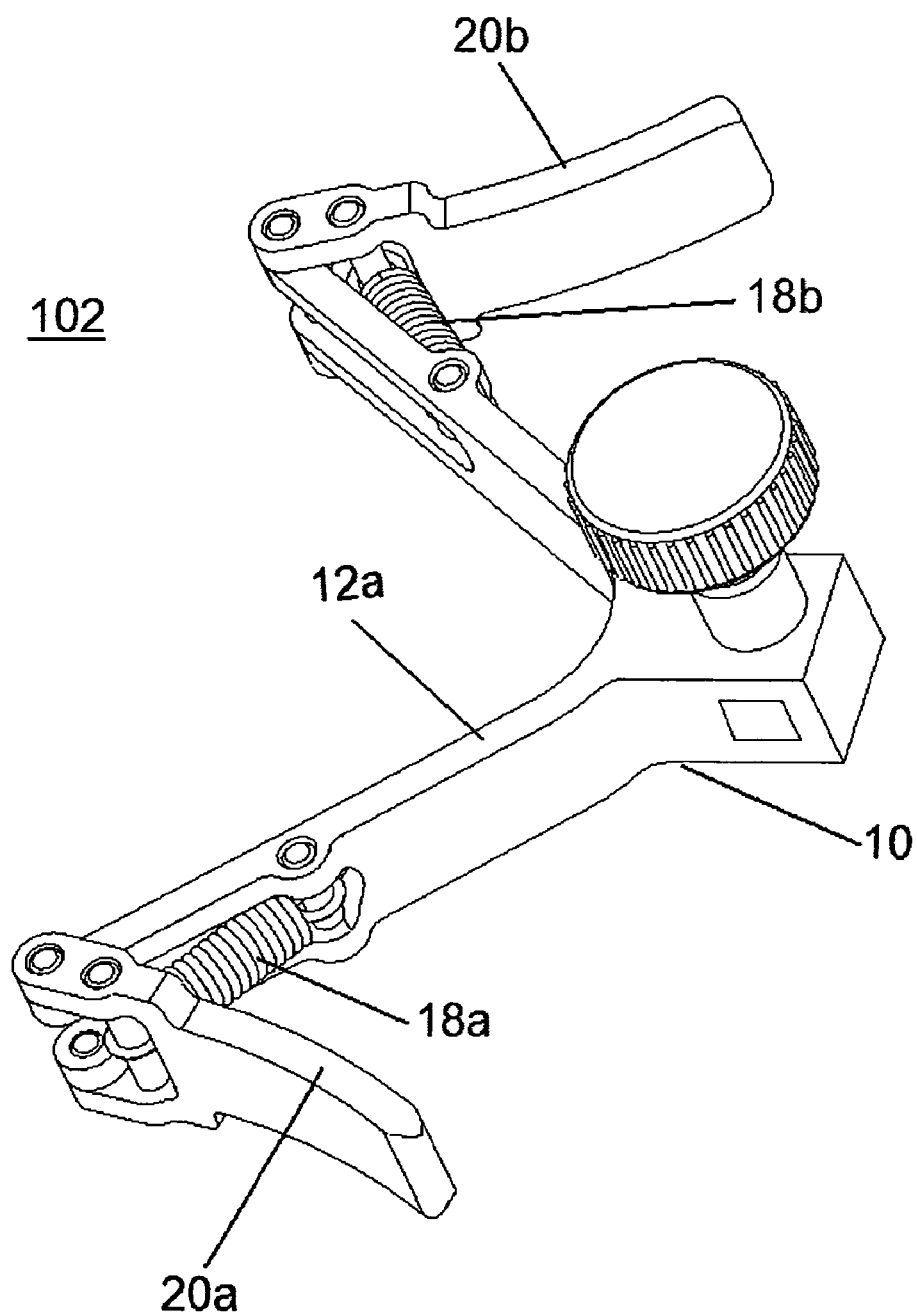
FIG. 3 is a perspective view of the ankle clamp of FIG. 2 in the open position.

FIG. 3 illustrates the position of the clamping arms 20a, 20b in the open position. The connection between the ankle clamp base arms 12a, 12b and the springs 18a, 18b can be configured to allow the clamping arms 20a, 20b to remain open when the ankle clamp 102 is in the open position. The ankle clamp design advantageously allows the user to toggle the ankle clamp from the open to close position and easily assemble the ankle clamp to the patient without the use of manual force to keep the clamp open during assembly to the patient. However, the present unicondylar tibial alignment guide embodiment can also be used with any conventional ankle clamp. Additional suitable ankle clamp designs are discussed in U.S. Pat. No. 5,197,944 to Steele, which is hereby incorporated by reference in its entirety.

Referring back to FIG. 1, the main shaft of the unicondylar tibial alignment guide 100 includes three sections, a top sliding section 114, a middle sliding section 110, and a bottom sliding section 112. The top and middle sliding sections 114, 110 slide into the bottom sliding section 112 in a telescoping-like manner. The bottom sliding section 112 has a middle slide clamp 126 that fixes or locks-in the position of the middle sliding section 110 relative to the bottom sliding section 112. The middle sliding section 110 has a top slide clamp 128 that fixes the position of the top sliding section 114 in a fixed position relative to the middle sliding section 110. The shape of the sliding sections can be of any suitable shape that allows one section to slide against or into another section. In the present embodiment, the middle slide clamp 126 can be positioned at the superior end of the bottom sliding section 112. The middle slide clamp 126 has a knob 130 for engaging a screw (not shown) and a casing 132 rigidly fixed to the bottom sliding section 112. The bottom sliding section 112 can be configured to have an I-shaped shaft. The middle sliding section 110 can be configured to have an elongated U-shape that slides against the inset region formed by the I-shaped shaft of the bottom sliding section 112. The top of the middle sliding section 110 can have a corresponding top slide clamp 128, similar to the middle slide clamp 126, about which the top sliding section 114 slides against. The top sliding section 114 can be configured to have an elongated rectangular shape and a curved top section 116. The top sliding section 114 can also be configured with a scale 134 for measuring the depth of a tibia resection as further described below and illustrated in FIG. 4. The unicondylar tibial alignment guide 100 can alternatively be configured with more than two telescoping sections.

Figure 4:
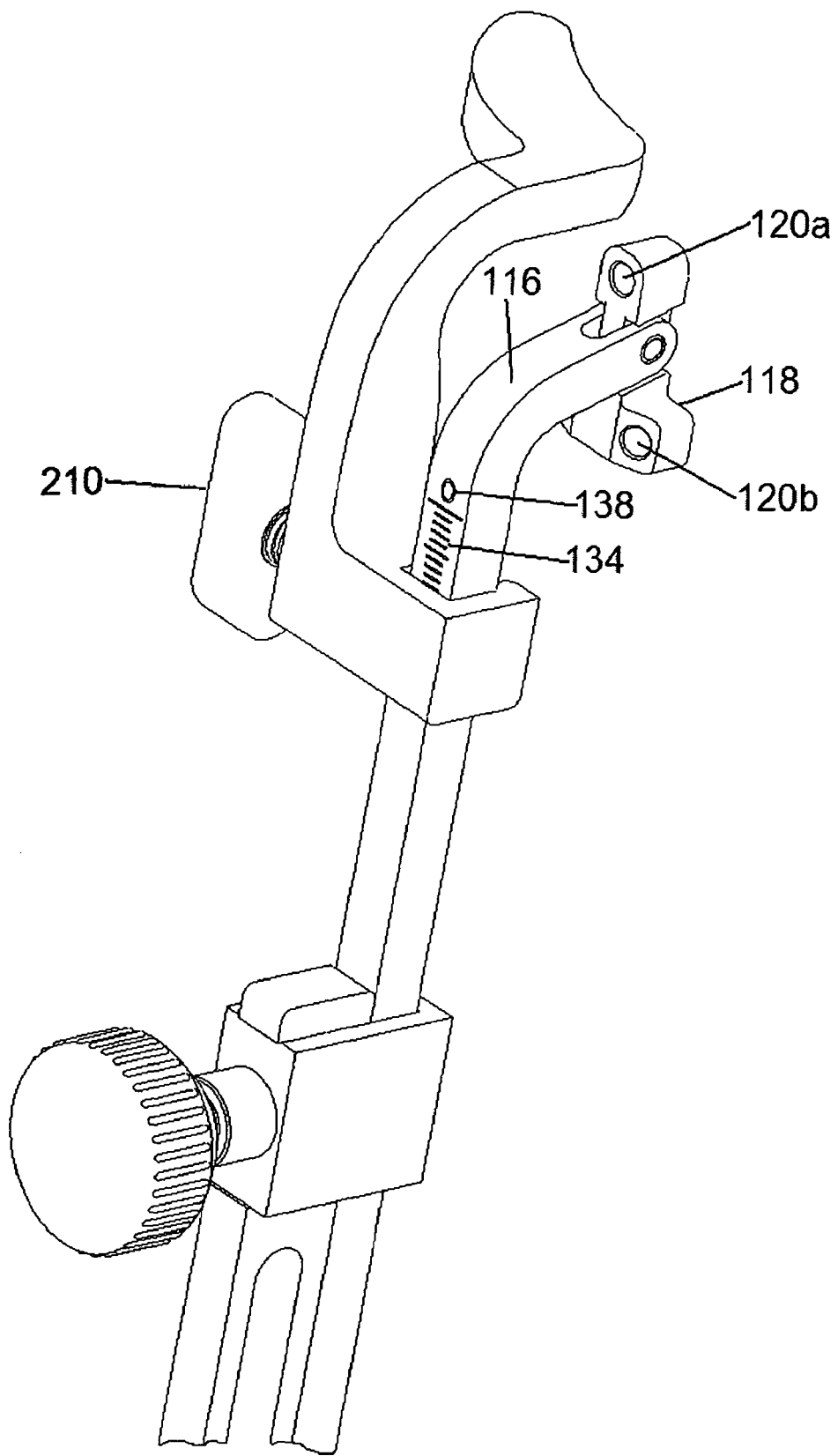
FIG. 4 is a perspective view of section 4 of FIG. 1 of the unicondylar tibial alignment guide assembled to the unicondylar tibial resection guide of FIG. 1.

Attached to the end of the curved top section 116 can be a pivoting lateral tibia anchor 118 as shown in FIG. 4. The pivoting lateral tibia anchor 118 has openings 120a, 120b, and 120c (not shown) that allows for a fixing element such as a fixation pin (not shown) to secure the lateral tibia anchor 118 to a tibia bone at a location where the lateral tibia anchor 118 contacts the tibia below the unicondylar tibial resection guide. The orientation of the openings 120a-c varies depending upon the pivot of the lateral tibia anchor 118. The pivoting lateral tibia anchor 118 can alternatively be configured to have any reasonable number of passages to allow for additional fixation pins to be used. Because the lateral tibia anchor 118 is pivotably attached to the unicondylar tibial alignment guide 100, the lateral tibia anchor 118 is operable to pivot the unicondylar tibial alignment guide 100 and/or the tibial resection guide 200 towards or away from the tibia bone.

Referring back to FIG. 1 the bottom sliding section 112 can be configured with a metatarsal pointer 106 at its most distal end. The bottom portion of the bottom sliding section 112 also has a substantially horizontal passage 108 that allows for the connecting rod 104 to slide in a substantially anterior/posterior direction. The position of the connecting rod 104 sliding about the horizontal passage 108 can be fixed in position by the flexion/extension clamp 124, similar to that of the middle slide clamp 126.

The connecting rod 104 connects the ankle clamp 102 and the bottom sliding section 112. The connecting rod 104 can be shaped to have two substantially orthogonal sliding ends 104a, 104b.

Figure 5:
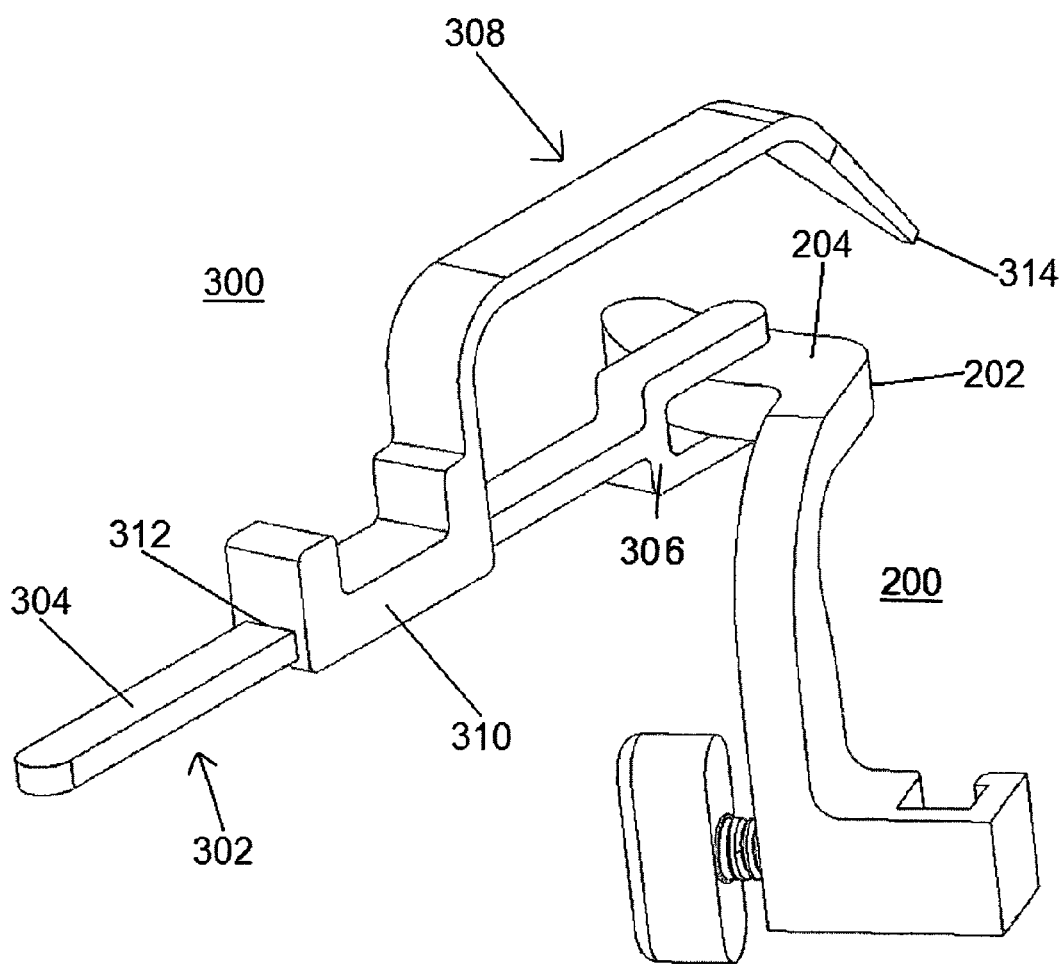
FIG. 5 is a perspective view of an embodiment of a tibial stylus assembled to the unicondylar tibial resection guide of FIG. 1.

FIG. 5 illustrates an embodiment of a tibial stylus 300 slidingly engaged with the unicondylar tibial resection guide 200. The tibial stylus 300 has a tibial stylus base 302 and a tibial stylus pointer 308. The tibial stylus base 302 can have an elongated base end 304 and a U-shaped connector end 306 for slidingly engaging the extended arm 202 of the unicondylar tibial resection guide 200. The tibial stylus pointer 308 can be shaped as shown in FIG. 5. The tibial stylus pointer 308 has a base member 310 and a tibial stylus point 314. The base member 310 has an opening 312 to allow the tibial stylus pointer 308 to slide along the length of the elongated base end 304 of the tibial stylus base 302. The position of the tibial stylus point 314 can be configured to be at about 0 mm above the surface of the unicondylar tibial resection guide cutting guide surface 204.

The tibial stylus base 302 engages the unicondylar tibial resection guide 200 by sliding engagement of the U-shaped connector end 306 along the open top surface of the extended arm 202 of the unicondylar tibial resection guide 200. The tibial stylus 300 is free to move anteriorly/posteriorly, medially/laterally, or to rotate internally and externally when assembled. The tibial stylus point 314 slides freely along the tibial stylus base 302. The overall assembly allows for the tip of tibial stylus point 314 to freely move along the entire surface of a proximal tibia.

In an alternative embodiment the tibial stylus can be configured as a single piece construct having a tibial stylus point and a magnetized base member. The base member therefore can be magnetically fixed to the cutting surface of the tibial resection guide. Thus, the tibial stylus, while semi-rigidly fixed to the surface of the tibial resection guide, can move freely along the plane of the unicondylar tibial resection guide, advantageously allowing the tibial stylus point to move freely along the entire surface of a proximal tibia.

In yet another embodiment, a tibial stylus can be configured for sliding engagement of the tibial stylus base along a top surface of a member. The member can be a cutting guide, flange, or any other structure configured to support the tibial stylus.

In operation, the unicondylar tibia resection guide 200 can be assembled to the top sliding section 114 as shown in FIG. 1. The unicondylar tibial resection guide 200 can be configured to slide proximally and distally along the top sliding section 114 of the unicondylar tibia alignment guide 100. Proximal and distal positioning can be fixed by use of the tibial resection guide locking screw clamp 210. The tibial stylus 300 can then be assembled to the unicondylar tibia resection guide 200 as shown in FIG. 5.

With the unicondylar tibia resection guide 200 and unicondylar tibia alignment guide 100 positioned against the anterior aspect of the knee, the tibial stylus point 314 is positioned on the proximal surface of the tibia, such as the sulcus, to indicate a zero reference point. The top sliding section 114 is then repositioned such that the unicondylar tibia resection guide 200 is set to the zero mark position 138 located on the scale 134 of the top sliding section 114. The unicondylar tibial resection guide 200 can be then secured to the unicondylar tibial alignment guide 100 and the pivoting tibia anchor 118 pinned (via opening 120a) to the proximal tibia by fixation pins (not shown) to provide a tibia reference point. After the unicondylar tibial resection guide 200 is fixed in position, the tibial stylus 300 can be removed. The unicondylar tibia alignment guide 100 however can advantageously remain in place for the distal and posterior resections, allowing the flexion space to be easily adjusted relative to the extension space by increasing or decreasing the tibia slope, if necessary, and allowing for the tibial resection to be made with the unicondylar tibial alignment guide 100 in position. Thus, overall alignment can be improved since the tibial resection can be simultaneously made with the unicondylar tibial alignment guide 100 in place.

An advantage of the present embodiment is that it allows for the user to easily adjust resection levels compared to commercial tibial resection systems which typically only allow for limited adjust means. The present embodiment also allows for ease in repositioning fixation pins or for adding additional fixation pins. In addition, the present embodiment allows for the tibial resection guide to be adjustable in three degrees of freedom, moving up and down (heaving), tilting up and down (pitching), and tilting side to side (rolling).

The length of the tibia alignment guide can be adjusted by extending or retracting the middle sliding section 110 and by extending or retracting the top sliding section 114. Having at least two telescoping sections allows for a greater range of length adjustment to accommodate for larger or smaller patients. Once the correct length is achieved the length adjustments can be locked in position by securing the middle slide clamp 126 and the top slide clamp 128.

The unicondylar tibia alignment guide 100 is free to rotate in a varus/valgus orientation about the pivoting tibial anchor (via a fixation pin through opening 120a) when the varus/valgus clamp 122 is not secured. Varus/valgus alignment can be accomplished by aligning the metatarsal pointer 106 with the second metatarsal bone and also by aligning the vertical axes of the metatarsal pointer 106, middle sliding section 110, and top sliding section 114 with the vertical axis of the tibia. Once varus/valgus alignment is achieved varus/valgus rotation can be fixed in position by securing the varus/valgus clamp 122. Varus/valgus constraint can be further enhanced by a second or third fixation pin (not shown) through additional passages or openings in the pivoting tibia anchor 118.

The unicondylar tibia alignment guide 100 is free to rotate in a flexion/extension orientation about the pivoting tibia anchor 118 when the flexion/extension clamp 124 is not tightened. Flexion/extension alignment can be achieved by referencing tibial slope. Accordingly, the unicondylar tibia alignment guide 100 can be rotated in the flexion/extension orientation until the cutting guide surface 204 of the unicondylar tibial resection guide 200 is parallel with the tibial slope. Once flexion/extension alignment is achieved flexion/extension rotation can be fixed by securing the flexion/extension clamp 124.

Figure 6:
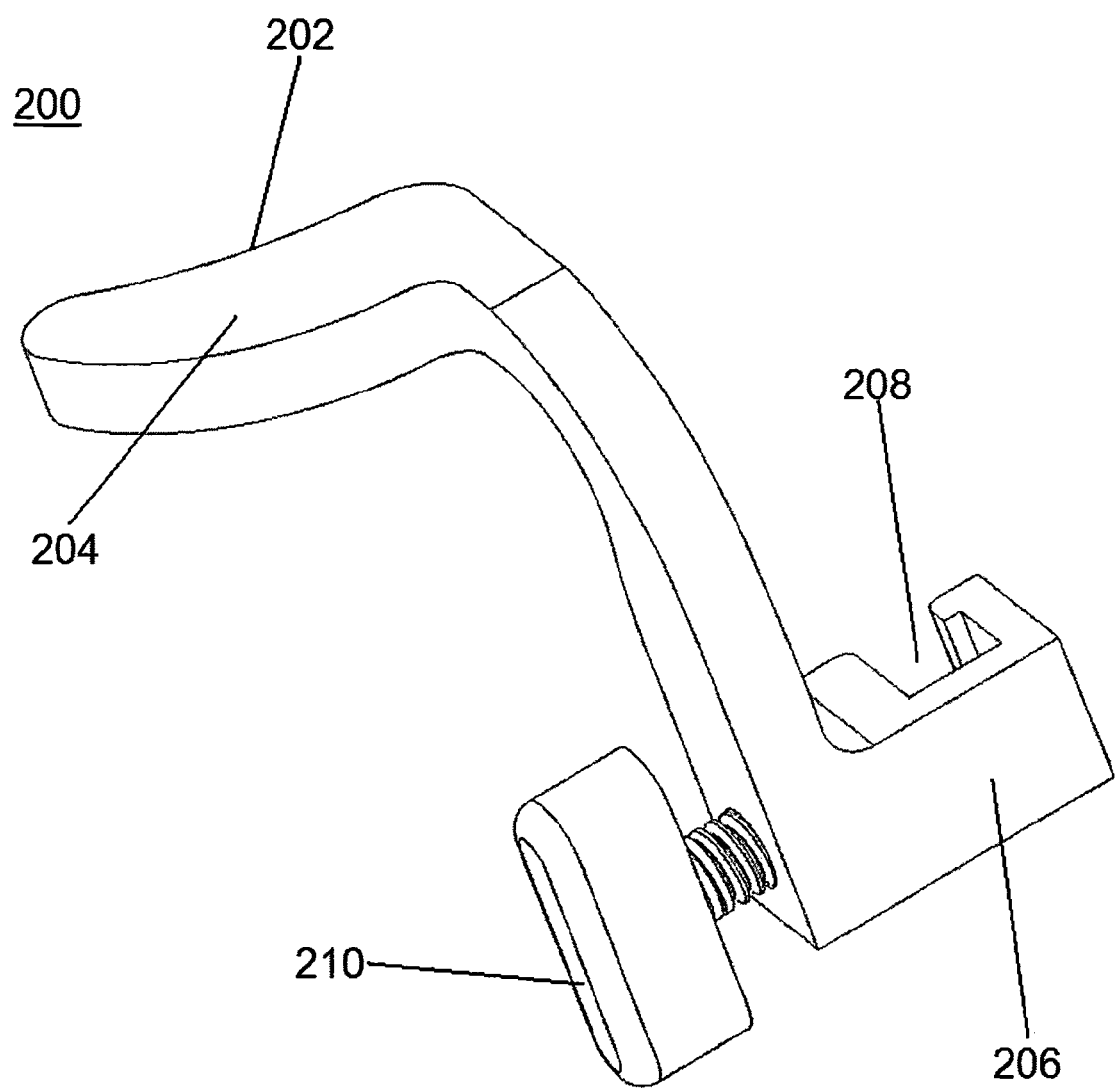
FIG. 6 is a perspective view of the unicondylar tibial resection guide of FIG. 1.

FIG. 6 illustrates an embodiment of a unicondylar tibial resection guide 200. The unicondylar tibial resection guide 200 includes an extended arm 202 having a cutting guide surface 204, a tibial resection guide base 206, and a tibial resection guide locking screw 210.

The extended arm 202 of the unicondylar tibial resection guide 200 has a planar cutting guide surface 204 that guides a cutting instrument such as a surgical saw blade. The posterior aspect of the extended arm 202 can be contoured to match the profile of an anterior tibial bone surface. The extended arm 202 can be connected to the tibial resection guide base 206. The extended arm 202 and the tibial resection guide base 206 can be a modular design or of a single piece design. The tibial resection guide base 206 has a substantially vertical passage 208 that allows for the guide base 206 to be assembled with the unicondylar tibial alignment guide 100. The locking screw 210 can be positioned orthogonally to the passage 208 to secure the unicondylar tibial resection guide 200 to the unicondylar tibial alignment guide 100 as shown in FIG. 4. The tibial resection guide base 206 of the unicondylar tibial resection guide 200 may be operable to adjust a distance between the tibial resection guide 200 and the lateral tibia anchor 118 as shown in FIGS. 4 and 6. An advantage of the present unicondylar tibial resection guide 200 embodiment is that the extended arm 202 having the cutting guide surface 204 can be made to any needed thickness. The overall thickness of the extended arm can be about 1 to about 100 mm or preferably about 2 to about 5 mm. Alternatively, the unicondylar tibial resection guide 200 can be configured with multiple cutting guide surfaces.

Figure 7:
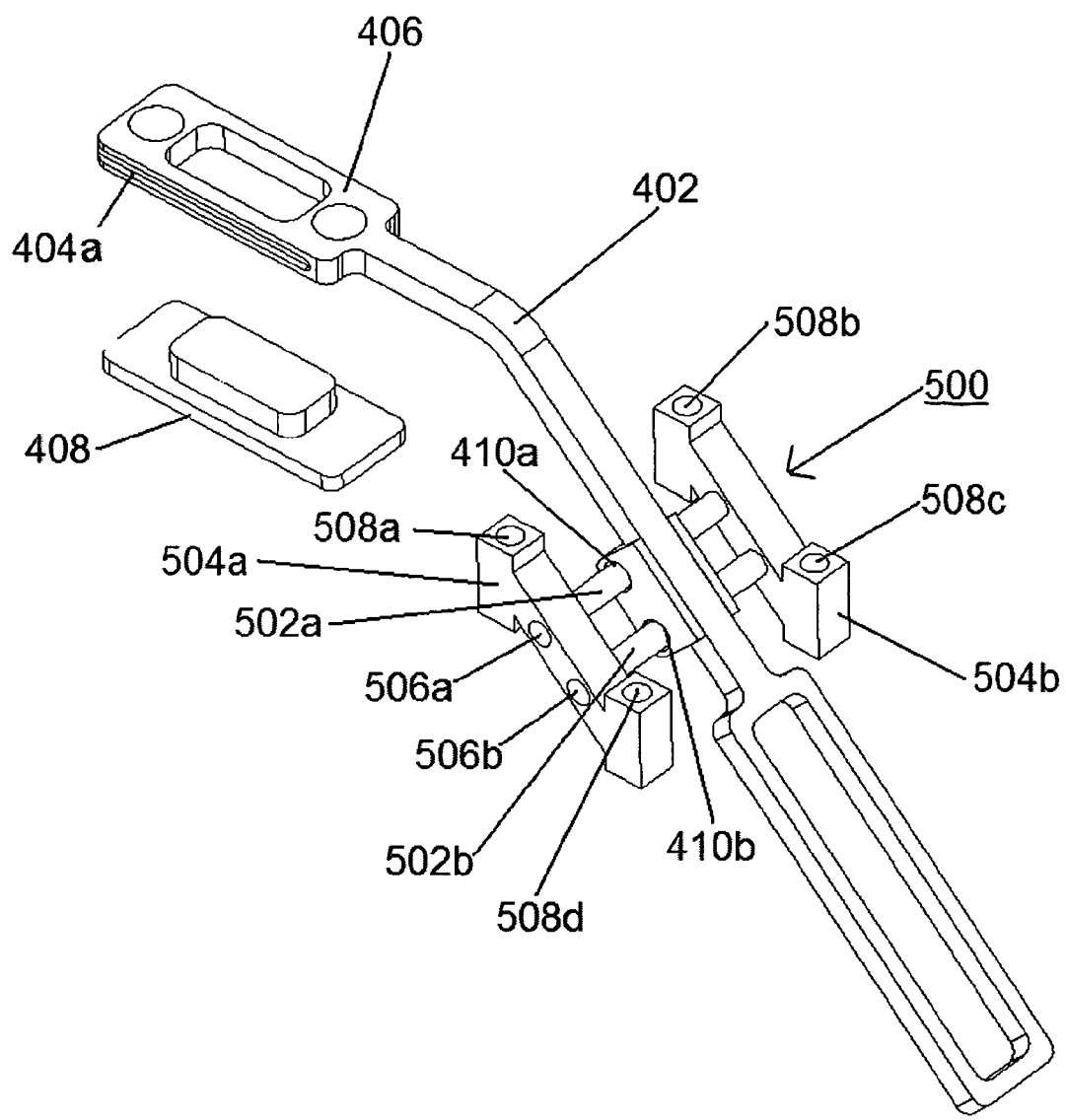
FIG. 7 is a perspective view of an embodiment of a knee joint instrument handle assembly of the present invention with an exploded view of a spacer block and base assembly.

FIG. 7 illustrates an embodiment of a knee joint instrument handle assembly 400. As shown in FIG. 7, the instrument handle assembly 400 includes an elongated handle 402, a base 406, and a spacer block 408. The elongated handle 402 can be curved downward to allow greater clearance for cutting instruments during use. The base 406 has a pair of slide tracks 404a and 404b (not shown). The spacer block 408 attaches to the base 406. In the present embodiment, the spacer block 408 attaches to the base 406 via magnetic attraction i.e., magnets. However, other similar mechanisms known in the art, such as ball plungers, detents, spring connectors, screws, snaps, and temporary epoxy, can also be used. The elongated handle 402 can also be configured to have two openings 410a, 410b for attaching an alignment rod holder 500.

The alignment rod holder 500 has two dowels 502a, 502b that pass through the two openings 410a, 410b in the alignment rod handle 402. The dowels 502a, 502b are connected to a first and second alignment rod holder base 504a, 504b having two dowel openings 506a, 506b. The alignment rod holder 500 can alternatively be configured with a single dowel and a single dowel opening. In the present embodiment, the alignment rod holder 500 can be configured to have four substantially vertical passages or openings 508a, 508b, 508c, 508d for supporting an alignment rod (not shown). In operation, the sliding alignment rod holder 500 slides substantially in the medial/lateral direction to allow the alignment rods to be positioned adjacent the anterior tibia when used in a unicondylar surgery of the medial or lateral compartment of the left or right knee. An advantage of the present embodiment of the knee joint instrument handle assembly and alignment rod holder is that the alignment rod can be placed directly anterior of the tibia, thus eliminating possible error such as parallax error, especially during unicondylar knee surgery.

Figure 8:
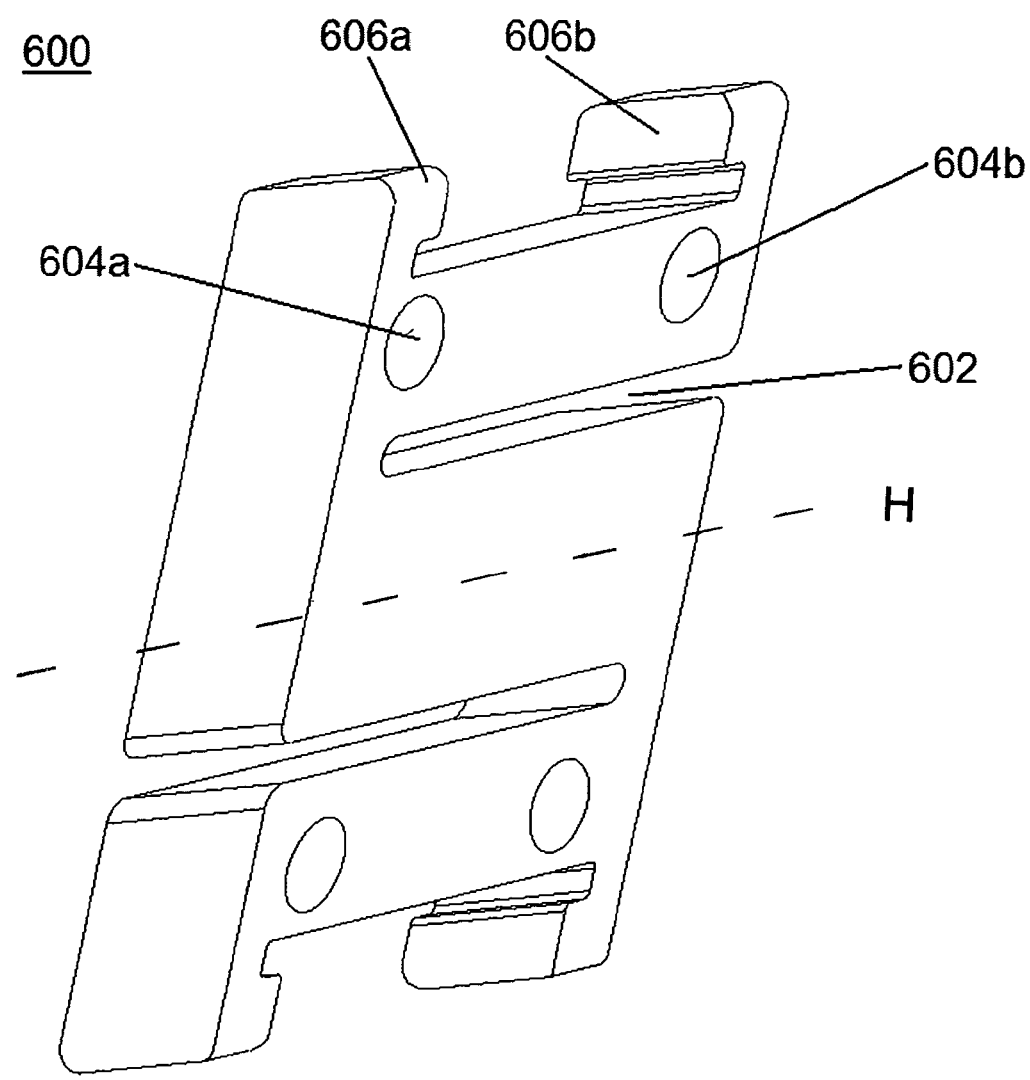
FIG. 8 is a perspective view of an embodiment of a unicondylar femoral distal resection guide of the present invention.

FIG. 8 illustrates an embodiment of a unicondylar femoral distal resection guide 600. The unicondylar femoral distal resection guide 600 has a channel 602 to guide the path of a cutting instrument, such as a surgical saw. The unicondylar femoral distal resection guide 600 can be configured to be reversible, such that it can be used for either the right or left knee while the open side of the channel 602 always faces the outside of the knee. The unicondylar femoral distal resection guide 600 can also be provided with openings 604a, 604b for the passage of a fixing element such as a fixation pin (not shown) to secure the cutting block to the distal femur. A pair of shoulders 606a, 606b are positioned on the ends of the unicondylar femoral distal resection guide 600 for sliding engagement with the slide tracks 404a, 404b of the instrument handle assembly 400. The unicondylar femoral distal resection guide 600 is symmetric about a horizontal plane H. In an alternative embodiment the unicondylar femoral distal resection guide can be provided with multiple channels for guiding a cutting instrument.

Figure 9:
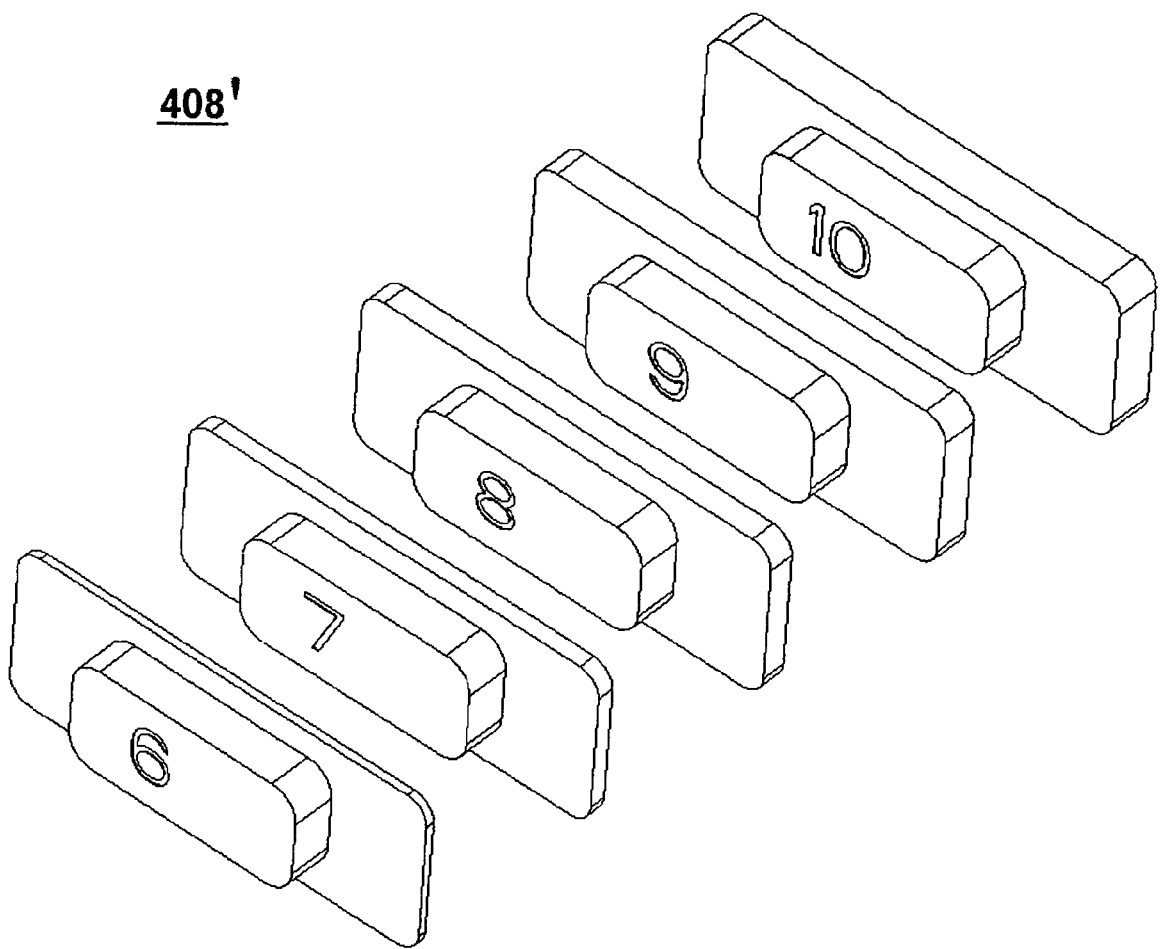
FIG. 9 is a perspective view of an embodiment of a series of spacer blocks of the present invention.

In operation, after a tibia has been prepared or resected, the instrument handle assembly 400, alignment rod holder 500, and unicondylar femoral distal resection guide 600 are assembled and positioned within the knee joint. A series of incrementally sized spacer blocks 408' as shown in FIG. 9, are then used to evaluate flexion and extension space after the tibia resection is made. Spacer block thicknesses are designed to represent the corresponding tibial implant thicknesses, which are typically incremented in whole millimeters, such as 6, 7, 8, 9, and 10 mm. Fixation pins (not shown) are then used to secure the unicondylar femoral resection guide 600 to the femur.

The knee joint instrument handle assembly 400 provides for easy removal from the knee joint even when the unicondylar femoral resection guide 600 is fixed to the femur manually or with pins. The positioning of the openings 604a, 604b in the unicondylar femoral resection guide 600 allows for easy access for the saw while the fixation pins are in place. Moreover, the distal femoral resection can be advantageously made with or without the knee joint spacer block in place. The unicondylar femoral distal resection guide 600 can be removably connectable or slidingly and removably connectable to the base 406. The unicondylar femoral distal resection guide 600 can be configured to operate concurrently and independently with the spacer block 408.

Figure 10:
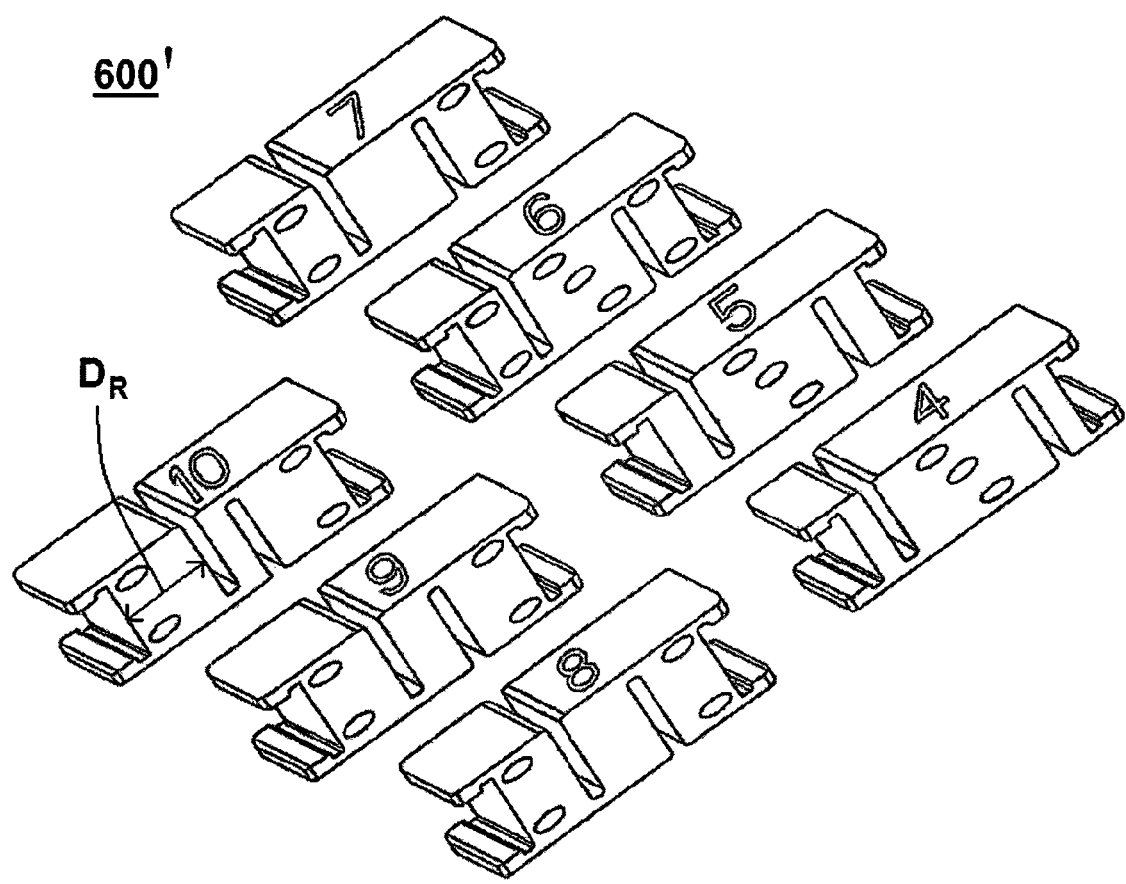
FIG. 10 is perspective view of an embodiment of a series of unicondylar femoral distal resection guides of the present invention.
Figure 11A:
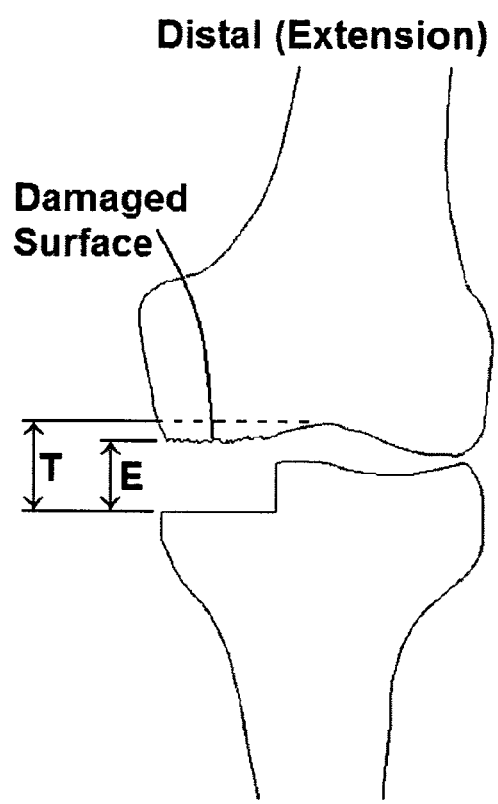
FIG. 11a is an anterior view of a knee joint at full extension with a damaged distal condyle surface and resected tibia.
Figure 11B:
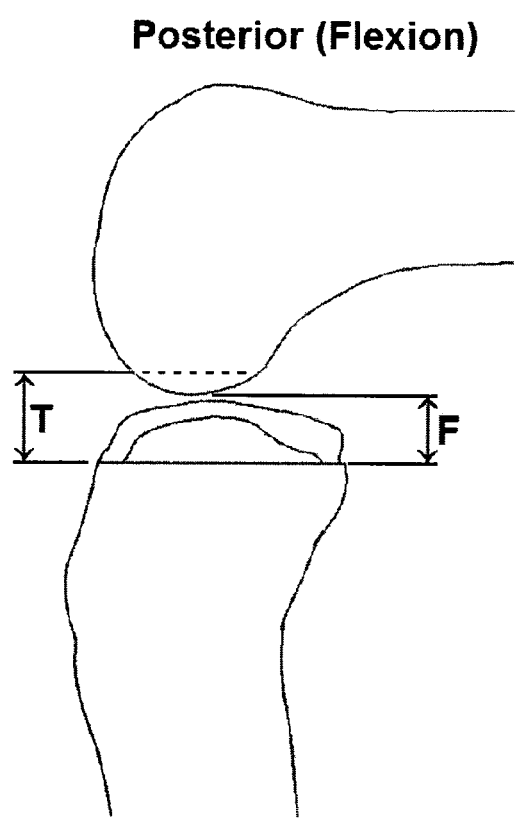
FIG. 11b is a side view of a knee joint at 90 degrees of flexion with a resected tibia.

A series of unicondylar femoral distal resection blocks 600' is shown in FIG. 10. Each unicondylar femoral distal resection block 600 can be configured to have a different femoral resection depth $D_R$ relative to the superior surface of the base 406. Accordingly, the resection level T, as shown in FIGS. 11a and 11b can be made with varying combinations of spacer blocks 408' and unicondylar femoral distal resection guides 600'.

Figure 13:
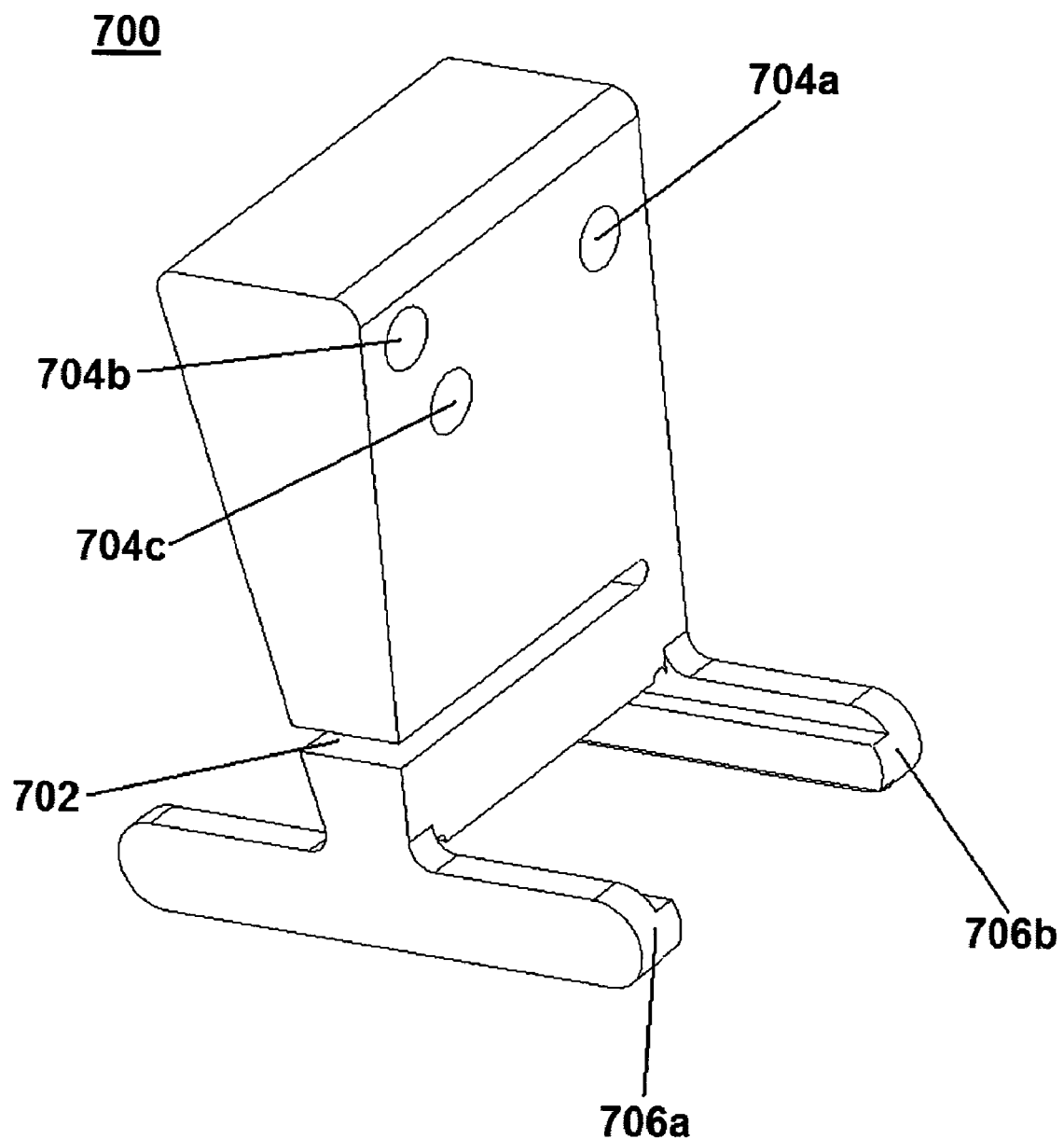
FIG. 13 is a perspective view of an embodiment of a unicondylar femoral posterior resection guide of the present invention.

FIG. 13 illustrates a unicondylar femoral posterior resection guide 700. Similar to the unicondylar femoral distal resection guide 600, the unicondylar femoral posterior resection guide 700 has a channel 702 to guide the path of a cutting instrument. The unicondylar femoral posterior resection guide 700 can be configured to be reversible, such that it can be used for either a right or left knee while the open side of the channel always faces the outside of the knee. The unicondylar femoral posterior resection guide 700 can also be provided with openings 704a, 704b, 704c for the passage of fixation pins (not shown) to secure the cutting block to the femur. A pair of shoulders 706a, 706b is positioned on the ends of the posterior resection guide for sliding engagement with the slide tracks 404a, 404b of the instrument handle assembly 400.

Figure 14:
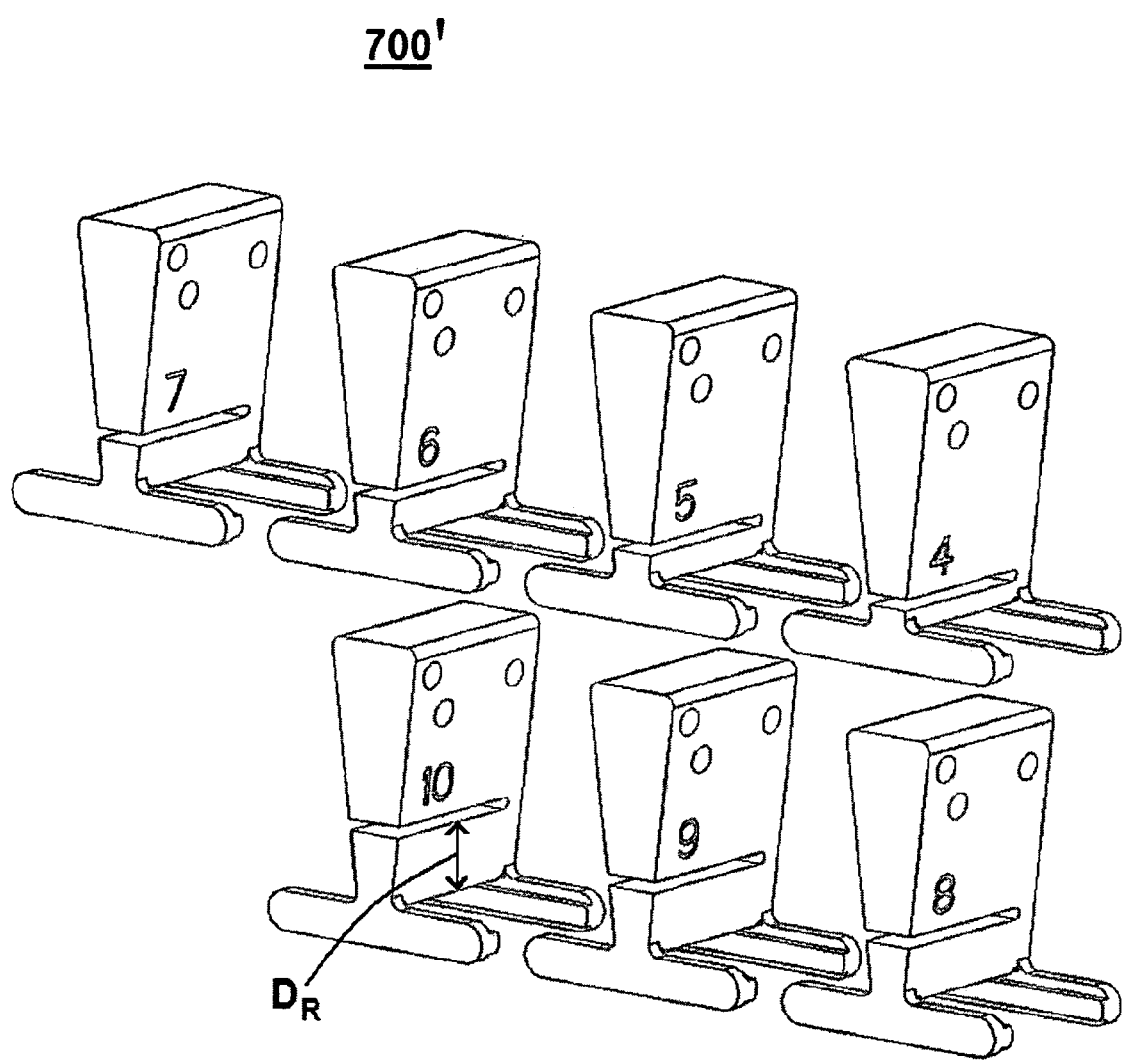
FIG. 14 is a perspective view of a series of unicondylar femoral posterior resection guides of the present invention.

The unicondylar femoral posterior resection guide 700 can be provided as a series of unicondylar femoral posterior resection guides 700' (FIG. 14), similar to the series of unicondylar femoral distal resection guides 600'. Likewise, each unicondylar femoral posterior resection guide 700 can be configured to have a different posterior resection depth $D_R$ relative to the superior surface of the base 406 (e.g., 4, 5, 6, 7, 8, 9, and 10 mm). The resection level T for making a distal resection can be made with varying combinations of spacer blocks 408' and unicondylar femoral posterior resection guides 700'.

Figure 12A:
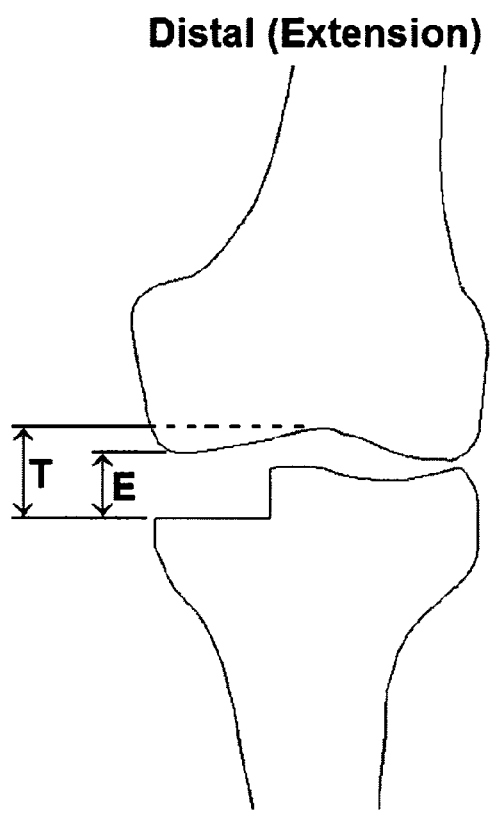
FIG. 12a is an anterior view of a knee joint at full extension with a resected tibia.
Figure 12B:
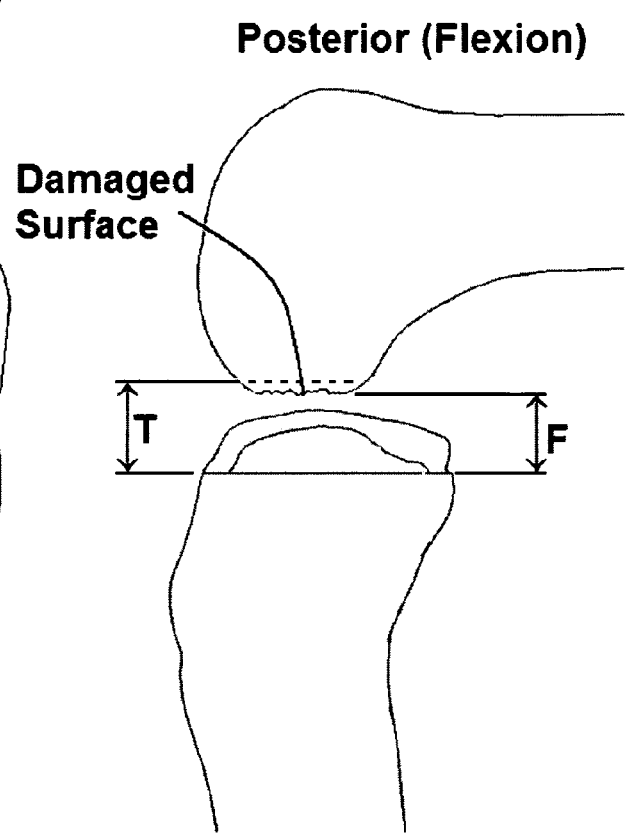
FIG. 12b is a side view of knee joint at 90 degrees of flexion with a damaged posterior condyle surface and resected tibia.

The present unicondylar knee instrument system allows for femoral resection depths to be determined based upon the knee joint pathology, i.e., the least affected or least damaged surface of the femoral knee. That is, if the distal surface of the femur is damaged (FIG. 11a), it would be desirable to reference off the posterior condyle to determine the appropriate spacer block/resection guide combination to use. Alternatively if the posterior surface of the femur is damaged (FIG. 12b), it would be desirable to reference off the distal condyle to determine the appropriate spacer block/resection guide combination to use.

For example, if the least affected site is the posterior condyle (FIG. 11b), the appropriate knee joint spacer block thickness needed to fill the flexion space F would be determined with knee in flexion. Once the appropriate spacer block thickness is determined, for example a 10 mm spacer block, then the overall thickness T can be determined taking into account the implant thickness, for example a 5 mm thick implant (i.e., a 5 mm resection guide is necessary). The appropriate spacer block thickness is one that properly balances the knee (i.e., collateral ligaments are not too tight or too loose). Thus, the proper spacer block/resection guide combination can be one that provides for an overall thickness T of 15 mm. Thereafter, the extension space E can be filled with an appropriate spacer block 400, (most likely a larger thickness than that necessary to fill the flexion space) and the appropriate distal resection guide can be selected to provide for an overall thickness of 15 mm. That is, if the necessary spacer block to fill the extension space E is 12 mm, then the appropriate distal resection guide would be 3 mm. Thus, the present unicondylar knee instrument system allows the user to compensate for diseased or damaged surfaces of the bone by choosing different size spacer blocks 408' and unicondylar femoral resection guides 700' and initially referencing off the least affected region of the femur (either distal or posterior) to provide for the most accurate restoration of the anatomic joint line.

Regardless of whether the distal femur is damaged or not, the distal resection is made first. Making the distal resection first allows for a much better angular reference surface to make the posterior resection later in the surgery.

An advantage of the present system is that the instrumented technique reduces the need for up-sizing or down-sizing the implant size as the bone resection and knee balancing steps are concurrently conducted. That is, the resection guides are used concurrently with the balancing and alignment instruments. This allows for greater accuracy in femoral resections and in balancing the knee joint, compared to conventional systems that make separate tibial and femoral resections that are not referenced off of each other. The present system also advantageously allows for determining the proper resection depth based upon the least affected condyle and then assembling the necessary combination of spacer block and resection block to provide the appropriate resection depth.

Figure 15:
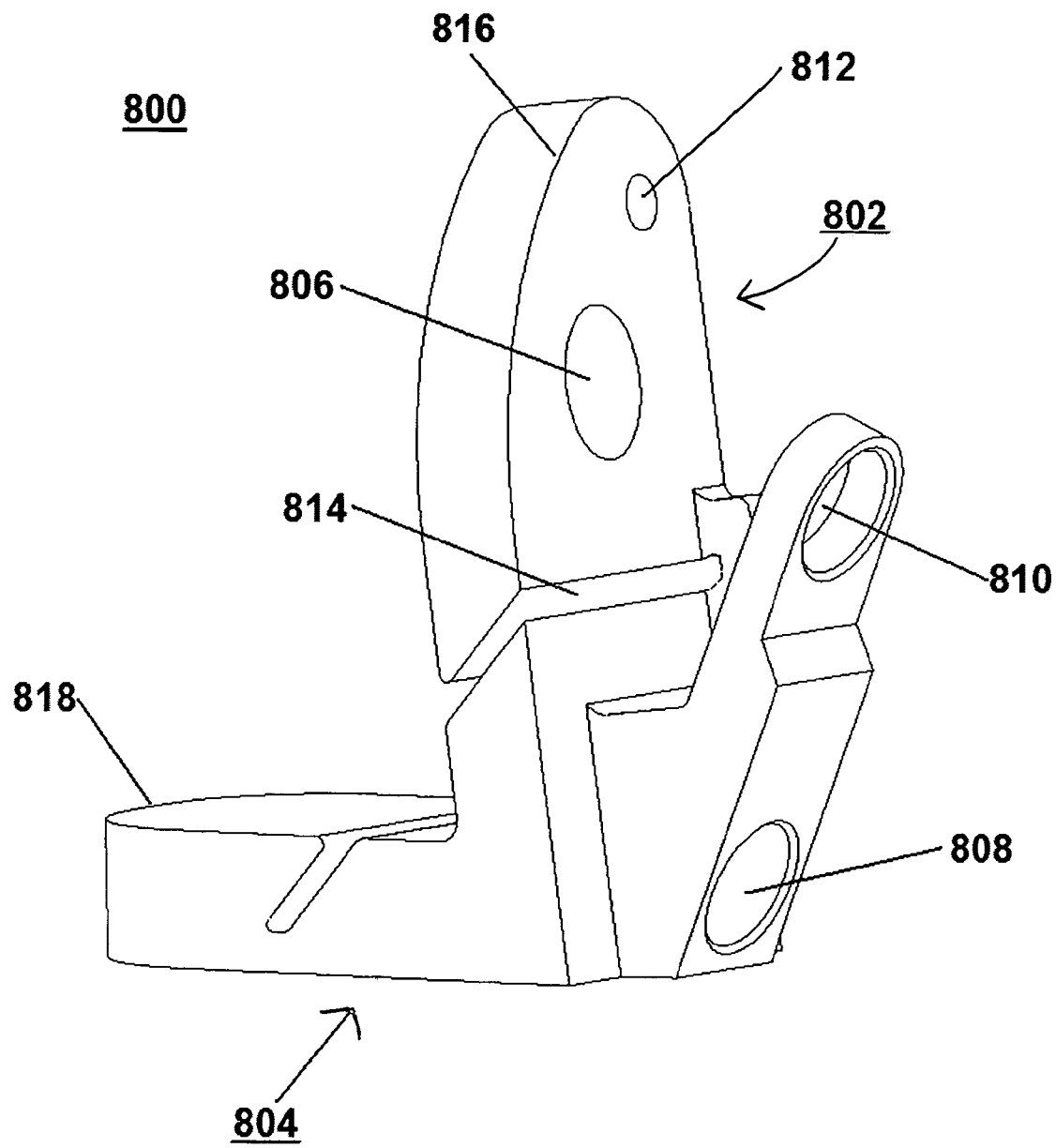
FIG. 15 is a perspective view of an embodiment of a unicondylar femoral chamfer and peg-hole guide of the present invention.

FIG. 15 illustrates an embodiment of a unicondylar femoral chamfer and peg-hole guide 800. The guide 800 can align a femoral chamfer cut on the distal femur and guides the drilling of peg holes for implanting a unicondylar femoral implant having pegs. The guide 800 can be L-shaped having a distal end 802 and a posterior end 804. The distal end 802 has two openings 806, 808 and a flange opening 810, for guiding a cutting instrument, such as a surgical drill, for making peg holes. The position of the openings 806, 808, 810 correspond to the position of peg holes on a corresponding unicondylar femoral knee implant having pegs. The distal end has an additional opening 812 for accepting a fixation pin (not shown) to secure the guide 800 to the distal femur. The opening 812 can be oriented to allow for easy saw and drill access when the fixation pin is in place. The unicondylar femoral chamfer and peg-hole guide 800 can also be configured to have multiple openings for accepting multiple fixation pins. A chamfer resection guide slot 814 extends from the distal end 802 to the posterior end 804 to guide a cutting instrument in making a chamfer cut on the distal femur to closely match that of a unicondylar femoral knee implant having a chamfer bone engaging surface.

In operation, a chamfer resection can be made using the chamfer resection guide slot 810 and a cutting instrument, such as a sagittal saw. The peg holes are made by using the peg-hole guides 806, 808, 810 and a cutting instrument, such as a step drill. The unicondylar femoral chamfer and peg-hole guide 800 can be fixed to the femur with at least one fixation pin.

Figure 16:
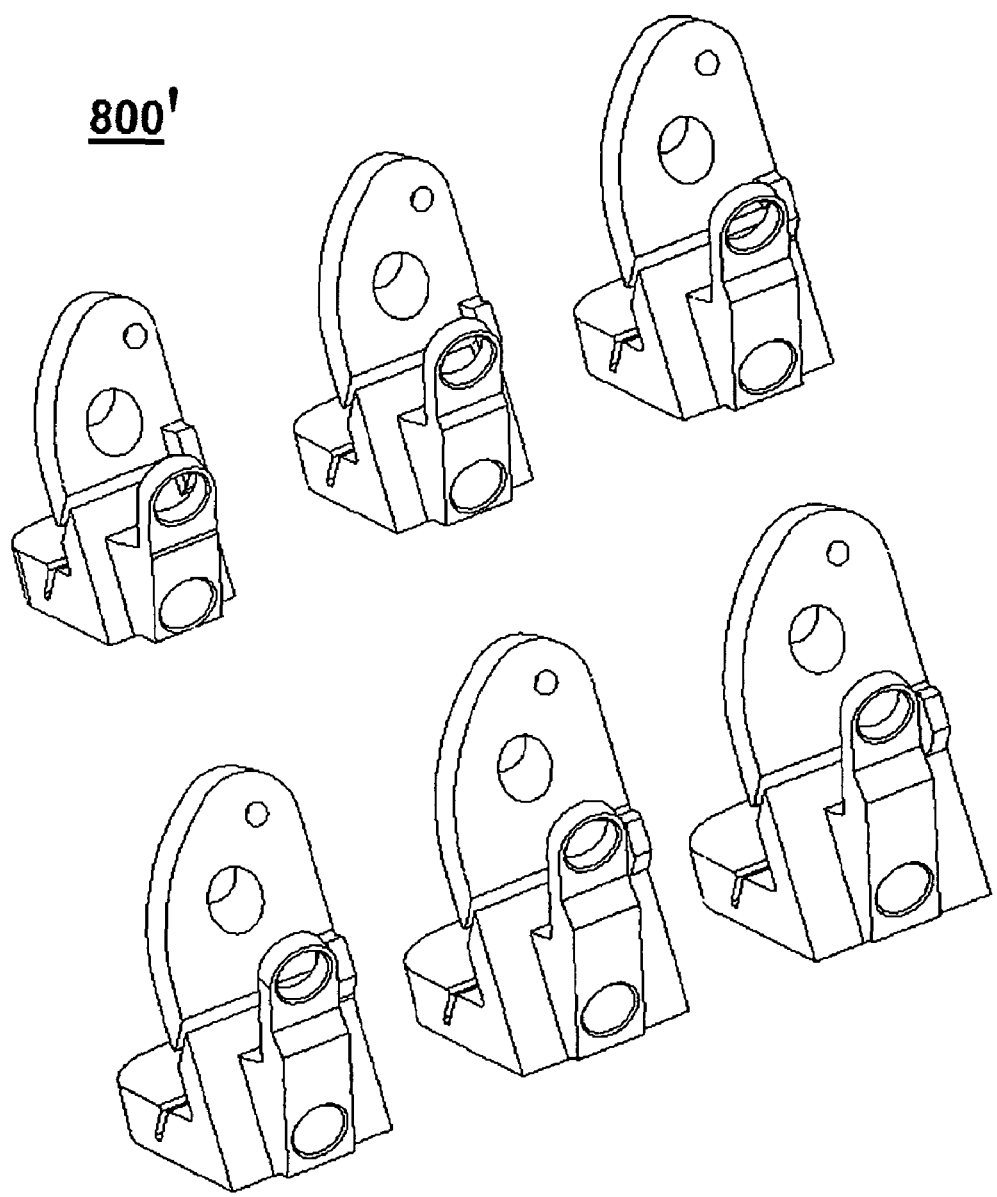
FIG. 16 is a perspective view of a series of femoral chamfer and peg hole guides of the present invention.

The chamfer and peg-hole guide 800 can also be used to size the femur and to determine the medial lateral position of the definitive implant. The distal and posterior resections are not size dependent thus, the user does not need to determine implant sizing until the last femoral resections are made i.e., femoral chamfer resection. The femoral chamfer cut is the only implant size dependent resection. The distal profile 816 closely matches the distal profile of the definitive implant to allow for proper sizing and medial/lateral positioning based upon fit and bone coverage. The posterior profile 818 also closely matches that of the definitive implant so that a check for overhang and coverage can be made. The unicondylar chamfer and peg hole guide can also be provided as a series of chamfer and peg hole guides 800', as shown in FIG. 16, similar to the series of unicondylar femoral distal resection guides 600'. Likewise, each chamfer and peg hole guide can be configured to match the resection levels of the corresponding unicondylar femoral distal 600' and unicondylar femoral posterior 700' resection guides.

Figure 17:
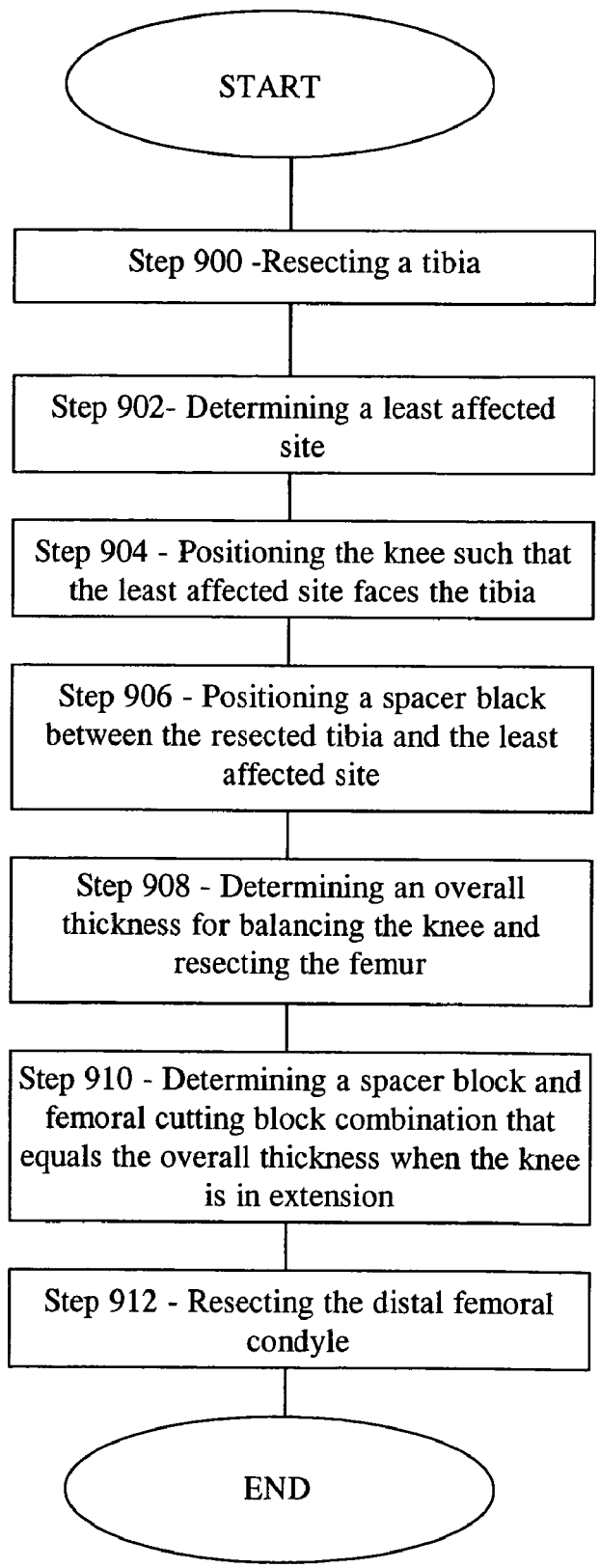
FIG. 17 is a flowchart of a method for preparing a femoral condyle for the implantation of a unicondylar knee implant.

The present unicondylar knee instrument system also provides for a method of preparing a femoral condyle of a knee for the implantation of a unicondylar femoral knee implant (as shown in FIG. 17) that includes the steps of resecting a tibia (Step 900), determining a least affected site (Step 902), wherein the site is a distal femoral condyle or a posterior femoral condyle, positioning the knee such that the least affected site faces the tibia (Step 904), positioning a spacer block between the resected tibia and the least affected site (Step 906). Then the step of determining an overall thickness for balancing the knee and resecting the femur to a thickness of a corresponding unicondylar femoral implant (Step 908), determining a spacer block and femoral cutting block combination that equals the overall thickness when the knee is in extension (Step 910), and resecting the distal femoral condyle (Step 912).

The embodiments of the present unicondylar knee instrument system are shown and described for purposes of illustration only and not for purposes of limitation. While there have been shown, described, and pointed out fundamental novel features of the invention as applied to several embodiments, it will be understood that various omissions, substitutions, and changes in the form and details of the devices illustrated, and in their operation, may be made by those skilled in the art without departing from the spirit and scope of the invention. Substitutions of elements from one embodiment to another are also fully intended and contemplated. It is also to be understood that the drawings are not necessarily drawn to scale, but that they are merely conceptual in nature. The invention is defined solely with regard to the claims appended hereto, and equivalents of the recitations therein.

The above mentioned patents, applications, and publications are hereby incorporated by reference in their entirety.

What is claimed is:

1. A method of preparing a femoral condyle of a femur for the implantation of a unicondylar femoral knee implant comprising the steps of:

resecting a tibia;

determining a least affected site, wherein the site is a distal femoral condyle or a posterior femoral condyle;

positioning the knee such that the least affected site faces the tibia;

positioning a spacer block between the resected tibia and the least affected site;

determining an overall thickness for balancing the knee and resecting the femur to a thickness of a corresponding unicondylar femoral implant;

determining a spacer block and unicondylar femoral cutting block combination that equals the overall thickness when the knee is in extension; and resecting the distal femoral condyle.

2. The method as recited in claim 1, wherein the step of resecting the distal femoral condyle includes the steps of:

providing an apparatus including an instrument handle assembly including an elongated handle having a base, removably connecting a spacer block to the base, removably connecting a unicondylar resection guide to the base that is configured to operate concurrently with the spacer block, guiding a cutting tool with at least one channel in the unicondylar resection guide, and receiving a fixing element in at least one opening of the unicondylar resection guide.

3. The method of claim 2, including the step of slidingly and removably connecting the unicondylar resection guide to the base.

4. The method of claim 2, wherein the spacer block and unicondylar resection guide are configured to operate independently of each other.

5. The method of claim 1, including the steps of aligning a unicondylar femoral resection guide, providing an instrument handle assembly having a base, and connecting an alignment rod holder to the instrument handle assembly that slides in a substantial medial and lateral direction.

6. The method of claim 5, including the step of removably connecting a unicondylar resection guide to the base.

7. The method of claim 5, including the steps of slidingly and removably connecting a unicondylar resection guide to the base.

8. The method of claim 5, including the step of removably connecting a spacer block to the base.

9. The method of claim 5, wherein the alignment rod holder includes a first alignment rod holder base having at least one substantially vertical passage and a second alignment rod holder base having at least one substantially vertical passage, the method including the step of connecting at least one dowel to the first and second alignment rod holder bases such that the first and second alignment rod holder bases slide within the instrument handle assembly in the substantially medial and lateral direction.

* * * * *